United States Patent
Fadhel et al.

(10) Patent No.: US 11,420,915 B2
(45) Date of Patent: Aug. 23, 2022

(54) RED MUD AS A CATALYST FOR THE ISOMERIZATION OF OLEFINS

(71) Applicant: Saudi Arabian Oil Company, Dhahran (SA)

(72) Inventors: Bandar A. Fadhel, Dhahran (SA); Mohammed A. Albuali, Dhahran (SA); Rami Bamagain, Dhahran (SA); Thamer Mohammad, Dhahran (SA); Munir D. Khokhar, Dhahran (SA); Wajdi Issam Al Sadat, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 250 days.

(21) Appl. No.: 16/899,254

(22) Filed: Jun. 11, 2020

(65) Prior Publication Data

US 2021/0387929 A1    Dec. 16, 2021

(51) Int. Cl.
| | |
|---|---|
| *C07C 5/25* | (2006.01) |
| *B01J 23/78* | (2006.01) |
| *B01D 3/14* | (2006.01) |
| *B01J 37/08* | (2006.01) |
| *C07C 7/04* | (2006.01) |
| *B01J 19/00* | (2006.01) |

(52) U.S. Cl.
CPC ............ *C07C 5/2506* (2013.01); *B01D 3/143* (2013.01); *B01J 19/00* (2013.01); *B01J 23/78* (2013.01); *B01J 37/08* (2013.01); *B01J 37/088* (2013.01); *C07C 5/2512* (2013.01); *C07C 7/04* (2013.01); *C07C 2521/06* (2013.01); *C07C 2523/04* (2013.01); *C07C 2523/78* (2013.01)

(58) Field of Classification Search
CPC .............................................. C07C 5/23–2593
See application file for complete search history.

(56) References Cited

U.S. PATENT DOCUMENTS

| | | | |
|---|---|---|---|
| 106,836 | A | 8/1870 | Kuhlmann |
| 665,346 | A | 1/1901 | Reed |
| 701,987 | A | 6/1902 | Alz |
| 978,576 | A | 12/1910 | Goodell |
| 2,378,905 | A | 6/1945 | Bates |
| 2,614,066 | A | 10/1952 | Cornell |
| 2,910,426 | A | 10/1959 | Gluesenkamp |
| 3,288,692 | A | 11/1966 | Leduc |

(Continued)

FOREIGN PATENT DOCUMENTS

| | | |
|---|---|---|
| CA | 2938299 | 5/2015 |
| CN | 104923234 | 12/2017 |

(Continued)

OTHER PUBLICATIONS

"Hydrogen and Oxygen production via electrolysis powered by renewable energies to reduce environmental footprint of a WWTP.," Greenlysis, URL <www.life-greenlysis.eu>, 16 pages, 2012.

(Continued)

*Primary Examiner* — In Suk C Bullock
*Assistant Examiner* — Alyssa L Cepluch
(74) *Attorney, Agent, or Firm* — Fish & Richardson P.C.

(57) ABSTRACT

A systems and a method for isomerizing a feedstock to form an alpha-olefin product stream are provided. An exemplary method includes calcining the red mud, flowing an olefin feedstock over the red mud in an isomerization reactor, and separating the alpha-olefin from a reactor effluent.

19 Claims, 3 Drawing Sheets

(56) References Cited

U.S. PATENT DOCUMENTS

| | | |
|---|---|---|
| 3,409,540 A | 11/1968 | Gould et al. |
| 3,427,235 A | 2/1969 | Leduc |
| 3,527,834 A | 9/1970 | Kehl et al. |
| 3,533,938 A | 10/1970 | Arnold |
| 3,585,217 A | 6/1971 | Titzenthaler |
| 3,632,497 A | 1/1972 | Leduc |
| 3,702,292 A | 11/1972 | Burich |
| 3,726,789 A | 4/1973 | Kovach |
| 3,755,143 A | 8/1973 | Hosoi et al. |
| 3,856,659 A | 12/1974 | Owen |
| 3,894,059 A | 7/1975 | Selvaratnam |
| 4,064,062 A | 12/1977 | Yurko |
| 4,090,949 A | 5/1978 | Owen et al. |
| 4,119,507 A | 10/1978 | Simmrock et al. |
| 4,134,824 A | 1/1979 | Kamm et al. |
| 4,230,551 A | 10/1980 | Salyer et al. |
| 4,264,435 A | 4/1981 | Read et al. |
| 4,297,203 A | 10/1981 | Ford et al. |
| 4,310,501 A | 1/1982 | Reh et al. |
| 4,332,663 A | 6/1982 | Bemeke |
| 4,426,276 A | 1/1984 | Dean et al. |
| 4,434,031 A | 2/1984 | Horowitz et al. |
| 4,522,802 A | 6/1985 | Setzer et al. |
| 4,527,003 A | 7/1985 | Okamoto et al. |
| 4,560,451 A | 12/1985 | Nielsen |
| 4,587,011 A | 5/1986 | Okamoto et al. |
| 4,602,986 A | 7/1986 | Ellis et al. |
| 4,655,904 A | 4/1987 | Okamoto et al. |
| 4,725,349 A | 2/1988 | Okamoto et al. |
| 4,735,728 A | 4/1988 | Wemhoff |
| 4,761,394 A | 8/1988 | Lauritzen |
| 4,786,400 A | 11/1988 | Farnsworth |
| 4,830,728 A | 5/1989 | Herbat et al. |
| 4,992,160 A | 2/1991 | Long et al. |
| 5,012,360 A | 4/1991 | Yamauchi et al. |
| 5,091,351 A | 2/1992 | Murakawa et al. |
| 5,108,581 A | 4/1992 | Aldridge |
| 5,527,436 A | 6/1996 | Cooker et al. |
| 5,601,937 A | 2/1997 | Isenberg |
| 5,624,493 A | 4/1997 | Wagh et al. |
| 5,904,837 A | 5/1999 | Fujiyama |
| 5,906,728 A | 5/1999 | Iaccino et al. |
| 5,951,850 A | 9/1999 | Ino et al. |
| 6,033,555 A | 3/2000 | Chen et al. |
| 6,084,142 A | 7/2000 | Yao et al. |
| 6,190,533 B1 | 2/2001 | Bradow et al. |
| 6,210,562 B1 | 4/2001 | Xie et al. |
| 6,280,593 B1 | 8/2001 | Wiese et al. |
| 6,293,979 B1 | 9/2001 | Choudhary et al. |
| 6,312,658 B1 | 11/2001 | Hufton et al. |
| 6,319,864 B1 | 11/2001 | Hannigan et al. |
| 6,336,791 B1 | 1/2002 | O'Toole |
| 6,531,515 B2 | 3/2003 | Moore, Jr. et al. |
| 6,656,346 B2 | 12/2003 | Ino et al. |
| 6,743,961 B2 | 6/2004 | Powers |
| 6,849,356 B2 | 2/2005 | Dow et al. |
| 6,852,901 B2 | 2/2005 | Hasenberg et al. |
| 6,979,757 B2 | 12/2005 | Powers |
| 7,019,187 B2 | 3/2006 | Powers |
| 7,045,554 B2 | 5/2006 | Raje et al. |
| 7,132,042 B2 | 11/2006 | Genetti et al. |
| 7,302,795 B2 | 12/2007 | Vetrovec |
| 7,374,664 B2 | 5/2008 | Powers |
| 7,378,561 B2 | 5/2008 | Olah et al. |
| 7,396,449 B2 | 7/2008 | Powers |
| 7,404,889 B1 | 7/2008 | Powers |
| 7,419,584 B2 | 9/2008 | Stell et al. |
| 7,460,333 B2 | 12/2008 | Akamatsu et al. |
| 7,550,642 B2 | 6/2009 | Powers |
| 7,592,290 B2 | 9/2009 | Hussain et al. |
| 7,642,292 B2 | 1/2010 | Severinsky |
| 7,744,747 B2 | 6/2010 | Halsey |
| 7,858,834 B2 | 12/2010 | Powers |
| 7,906,559 B2 | 3/2011 | Olah et al. |
| 7,972,498 B2 | 7/2011 | Buchanan et al. |
| 7,973,087 B2 | 7/2011 | Kibby et al. |
| 8,152,973 B2 | 4/2012 | Yamamoto et al. |
| 8,198,338 B2 | 6/2012 | Shulenberger et al. |
| 8,287,716 B2 | 10/2012 | Al-Sadah |
| 8,303,917 B2 | 11/2012 | Miyashiro et al. |
| 8,304,567 B2 | 11/2012 | Kadota et al. |
| 8,628,668 B2 | 1/2014 | Simonson |
| 8,816,137 B2 | 8/2014 | Olah et al. |
| 8,845,940 B2 | 9/2014 | Niven et al. |
| 8,951,333 B2 | 2/2015 | Cabourdin et al. |
| 9,085,497 B2 | 7/2015 | Jennings |
| 9,090,543 B2 | 7/2015 | Schoedel et al. |
| 9,096,806 B2 | 8/2015 | Abba et al. |
| 9,175,409 B2 | 11/2015 | Sivasankar et al. |
| 9,221,027 B2 | 12/2015 | Kuppler et al. |
| 9,242,230 B2 | 1/2016 | Moon et al. |
| 9,255,230 B2 | 2/2016 | Shafi et al. |
| 9,260,366 B2 | 2/2016 | Verhaak et al. |
| 9,279,088 B2 | 3/2016 | Shafi et al. |
| 9,284,497 B2 | 3/2016 | Bourane et al. |
| 9,284,502 B2 | 3/2016 | Bourane et al. |
| 9,296,961 B2 | 3/2016 | Shafi et al. |
| 9,303,323 B2 | 4/2016 | DiMascio et al. |
| 9,312,454 B2 | 4/2016 | Itoh et al. |
| 9,328,035 B1 | 5/2016 | Kuhn et al. |
| 9,435,404 B2 | 9/2016 | Goleski et al. |
| 9,555,367 B2 | 1/2017 | Masel et al. |
| 9,559,375 B2 | 1/2017 | Savinell et al. |
| 9,618,264 B1 | 4/2017 | Berdut-Teruel |
| 9,634,343 B2 | 4/2017 | Munier et al. |
| 9,675,979 B2 | 6/2017 | Hassell |
| 9,752,080 B2 | 9/2017 | Christensen et al. |
| 9,884,313 B2 | 2/2018 | Shen et al. |
| 9,963,392 B2 | 5/2018 | Deo et al. |
| 9,970,804 B2 | 5/2018 | Khousa et al. |
| 9,973,141 B2 | 5/2018 | Hammad et al. |
| 10,179,733 B2 | 1/2019 | Becker et al. |
| 10,252,243 B2 | 4/2019 | Fadhel et al. |
| 10,252,909 B2 | 4/2019 | Lofberg et al. |
| 10,329,676 B2 | 6/2019 | Kaczur et al. |
| 10,357,759 B2 | 7/2019 | D'Souza et al. |
| 10,422,754 B2 | 9/2019 | Al Hosani et al. |
| 2005/0211603 A1 | 9/2005 | Guillaume et al. |
| 2006/0171065 A1 | 8/2006 | Akamatsu et al. |
| 2008/0011644 A1 | 1/2008 | Dean |
| 2008/0011645 A1 | 1/2008 | Dean |
| 2008/0083648 A1 | 4/2008 | Bishop et al. |
| 2008/0194900 A1 | 8/2008 | Bhirud |
| 2008/0277314 A1 | 11/2008 | Halsey |
| 2008/0283445 A1 | 11/2008 | Powers |
| 2009/0050523 A1 | 2/2009 | Halsey |
| 2010/0089795 A1 | 4/2010 | Fujiyama et al. |
| 2010/0137458 A1 | 6/2010 | Erling |
| 2011/0021858 A1 | 1/2011 | Ramachandran et al. |
| 2011/0083996 A1 | 4/2011 | Shafi et al. |
| 2011/0132770 A1 | 6/2011 | Sala et al. |
| 2011/0247500 A1 | 10/2011 | Akhras et al. |
| 2013/0129610 A1 | 5/2013 | Kale |
| 2013/0220884 A1 | 8/2013 | Bourane et al. |
| 2013/0233766 A1 | 9/2013 | Shafi et al. |
| 2013/0248419 A1 | 9/2013 | Abba |
| 2015/0225295 A1 | 8/2015 | Mcandlish et al. |
| 2015/0337445 A1 | 11/2015 | Hasegawa et al. |
| 2015/0343416 A1 | 12/2015 | Fadhel et al. |
| 2016/0002035 A1 | 1/2016 | Ralston et al. |
| 2016/0264886 A1 | 9/2016 | Davydov |
| 2016/0333487 A1 | 11/2016 | Rodriguez |
| 2017/0050845 A1 | 2/2017 | Lofberg et al. |
| 2017/0292197 A1 | 10/2017 | Lei et al. |
| 2018/0057423 A1 | 3/2018 | Kimura et al. |
| 2019/0194074 A1 | 6/2019 | Amr et al. |

FOREIGN PATENT DOCUMENTS

| | | |
|---|---|---|
| DE | 102006020843 | 11/2007 |
| WO | WO 2000009633 | 2/2000 |
| WO | WO 2009073436 | 6/2009 |
| WO | WO 2010009077 | 1/2010 |
| WO | WO 2010009082 | 1/2010 |

(56) References Cited

FOREIGN PATENT DOCUMENTS

| | | |
|---|---|---|
| WO | WO 2010009089 | 1/2010 |
| WO | WO 2010143783 | 12/2010 |
| WO | WO 2015128045 | 9/2013 |
| WO | WO 2014160168 | 10/2014 |
| WO | WO 2015183200 | 12/2015 |
| WO | WO 2016207892 | 12/2016 |
| WO | WO 2019112555 | 6/2019 |

OTHER PUBLICATIONS

Albrecht et al., "Unexpectedly efficient CO2 hydrogenation to higher hydrocarbons over non-doped Fe2O3," Applied Catalysis B: Environmental 204: 119-126, May 2017, 8 pages.

Bhuiyan, "Metathesis of Butene to Produce Propylene over Mesoporous Tungsten Oxide Catalyst: Synthesis, Characterization and Kinetic Modeling," A Thesis Presented to the Deanship of Graduate Studies, King Fahd University of Petroleum and Minerals, in Partial Fulfillment of the Requirements for the Degree of Master of Science in Chemical Engineering, Jun. 2013, 188 pages.

Chew et al., "Effect of nitrogen doping on the reducibility, activity and selectivity of carbon nanotube-supported iron catalysts applied in CO2 hydrogenation," Applied Catalysis A: General 482: 163-170, Jul. 2014, 29 pages.

Choi et al., "Carbon dioxide Fischer-Tropsch synthesis: A new path to carbon-neutral fuels," Applied Catalysis B: Environmental 202: 605-610, Mar. 2017, 6 pages.

Choi et al., "Hydrogenation of carbon dioxide over alumina supported Fe—K catalysts," Catalysis Letters 40: 115-118, Mar. 1996, 4 pages.

Cowie et al., "Naturally occurring radioactive material and naturally occurring mercury assessment of black powder in sales gas pipelines," Radiation Protection and Environment 42: 34-9, Jan.-Mar. & Apr.-Jun. 2019, 6 pages.

Cramer et al., "The Mechanism of Isomerization of Olefins with transition metal catalysts," Journal of the American Chemical Society, 88(15): 3534-3544, Aug. 5, 1966, 11 pages.

Dinesh et al., "Iron-based flow batteries to store renewable energies," Environmental Chemistry Letters, Feb. 2018, 12 pages.

Ding et al., "CO2 Hydrogenation to Hydrocarbons over Iron-Based Catalyst: Effects of Physico-Chemical Properties of Al2O3 Supports," I&EC Research, Industrial & Engineering Chemistry Research 53(45): 17563-17569, Oct. 2014, 30 pages.

Du et al., "Sodium Hydroxide Production from Seawater Desalination Brine: Process Design and Energy Efficiency," Environmental Science & Technology 52: 5949-5958, 2018, 10 pages.

Godoy et al., "210Pb content in natural gas pipeline residues ("black-powder") and its correlation with the chemical composition," Journal of Environmental Radioactivity 83: 101-111, 2005, 12 pages.

Grafe et al., "Bauxite residue issues: IV. Old obstacles and new pathways for in situ residue bioremediation," Hydrometallurgy 108: 46-59, 2011, 14 pages.

Hu et al., "Hydrothermally stable MOFs for CO2 hydrogenation over iron-based catalyst to light olefins," Journal of CO2 Utilization, 15: 89-95, 2016, 7 pages.

Hua et al., "Transformation of 2-Butene into Propene on WO3/MCM-48: Metathesis and Isomerization of n-Butene," Catalysts 8: 585, 2018, 11 pages.

Lee et al., "Selective Positional Isomerization of 2-Butene over Alumina and La-promoted Alumina Catalysts," J. Ind. Eng. Chem. 13(7): 1062-1066, Dec. 2007, 5 pages.

Liu et al. "Fe—MOF-derived highly active catalysts for carbon dioxide hydrogenation to valuable hydrocarbons," Journal of CO2 Utilization 21:100-107, Oct. 2017, 8 pages.

Liu et al., "Pyrolyzing ZIF-8 to N-doped porous carbon facilitated by iron and potassium for CO2 hydrogenation to value-added hydrocarbons," Journal of CO2 Utilization 25: 120-127, May 2018, 8 pages.

Madadkhani, "Red mud as an Ironbased Catalyst for Catalytic Cracking of Naphthalene," a Thesis Submitted in Partial Fulfillment of the Requirement for the Degree of Master of Applied Science in the Faculty of Graduate and Postdoctoral Studies (Chemical and Biological Engineering), The University of British Columbia, Dec. 2016, 192 pages.

Morrison, "Cis-trans Isomerization of Olefins by Intramolecular Energy Transfer," Journal of the American Chemical Society 87(4): 932, Feb. 1965, 1 page.

Naik et al. "Carbon Dioxide sequestration in cementitious products," Report No. CNU-2009-02, REP-640, Department of Civil Engineering and Mechanics, College of Engineering and Applied Science, University of Wisconsin-Milwaukee, Jan. 2009, 53 pages.

Nam et al., "Catalytic conversion of carbon dioxide into hydrocarbons over iron supported on alkali ion-exchanged Y-zeolite catalysts," Applied Catalysis A: General 179: 155-163, Apr. 1999, 9 pages.

Nam et al., "Catalytic Conversion of Carbon dioxide into hyrdrocarbons over zinc promoted iron catalysts," Energy onvers. Manage. 38: S397-S402, 1997, 6 pages.

Ndlela et al., "Reducibility of Potassium-Promoted Iron Oxide under Hydrogen Conditions," Ind. Eng. Chem. Res. 42: 2112-2121, 2003, 10 pages.

Numpilai et al., "Pore size effects on physicochemical properties of Fe-Co/K-Al2O3 catalysts and their catalytic activity in CO2 hydrogenation to light olefins," Applied Surface Science 483: 581-592, Jul. 2019, 12 pages.

Pall.com [online], "Cyclo-Filter System," retrieved from URL <https://www.pall.com/en/oil-gas/midstream/midstream-black-powder.html>, retrieved on Jun. 16, 2020, available on or before 2020, 4 pages.

Pavlov et al., "Processes of Synthesis of 1-Butene from 2-Butene by the Positional Isomerization on Suffocation Exchangers," Russian Journal of Applied Chemistry 82:6 (1117-1122), Jul. 2009, 6 pages.

Ramirez et al., "Metal Organic Framework-Derived Iron Catalysts for the Direct Hydrogenation of CO2 to Short Chain Olefins," ACS Catalysis 8:9174-9182, 2018, 32 pages.

Russkikh et al., "Red mud as an efficient catalyst in turning CO2 hydrogenation," Chemical Science Seminar, retrieved from URL: <https://pse.kaust.edu.sa/events/red-mud-as-an-efficient-catalyst-in-turning-co2-hydrogenationinto-useful-products>, Oct. 13, 2019, Kaust, 2019, 1 page, (abstract only).

Shop.pall.com (online), "Black Powder Filter," retrieved from URL <https://shop.pall.com/us/en/search?SearchTerm=black+powder+filter&resetsearch=true>, retrieved on Jun. 16, 2020, available on or before 2020, 7 pages.

Thach et al., "Further Improvements in Isomerization of Olefins in Solvent-free conditions," retrieved from URL: <https://WWW.tandfonline.com/doi/abs/10.1080/00397919308011226>, Journal of Synthetic Communications 23:10 (1379-1384), Nov. 1992, 3 pages, (abstract only).

Van Beurden, "On the Catalytic Aspects of Stream-Methane Reforming: A Literature Survey," ECN-I—04-003, retrieved from URL: <https://publicaties.ecn.nl/PdfFetch.aspx?nr=ECN-I—04-003>, Dec. 2004, 27 pages.

Visconti et al., "CO2 Hydrogentation to Lower Olefins on a High Surface Area K-Promoted Bulk FE-Catalyst," Applied Catalyysis B: Environmental 200:530-542, 2017, 44 pages.

Wahyudi et al., "Utilization of Modified Red Mud as a Heterogeneous Base Catalyst for Transesterification of Canola Oil," Journal of Chemical Engineering of Japan 50(7): 561-567, Jul. 2017, 8 pages.

Wang et al., "Fe—Cu Bimetallic Catalysts for Selective CO2 Hydrogenation to Olefin-rich C2+ Hydrocarbons," I&EC Research, Industrial & Engineering Chemistry Research 57(13): 4535-4542, Feb. 2018, 37 pages.

Wei et al., "New insights into the effect of sodium on Fe3O4-based nanocatalysts for CO2 hydrogenation to light olefins," Catalysis Science & Technology 6(13): 4786-4793, 2016, 8 pages.

Yensen et al., "Open source all-iron battery for renewable energy storage," HardwareX 6: e00072, 2019, 11 pages.

(56) References Cited

OTHER PUBLICATIONS

You et al., "Hydrogenation of carbon dioxide to light olefins over non-supported iron catalyst," Chinese Journal of Catalysis 34(5): 956-963, May 2013, 8 pages.
U.S. Appl. No. 17/140,242, filed Jan. 4, 2004, Fadhel et al.
Fang et al., "A Nanomesoporous Catalyst from Modifier Red Mud and Its Application for Methane Decomposition to Hydrogran Production," Article ID 6947636, Hindawi Publishing Corporation, Journal of Nanomaterials, 2016, 8 pages.
Kurtoglu and Uzun, "Red Mud as an Efficient, Stable, and Cost-Free Catalyst for Cox-Free Hydrogren Production from Ammonia," Scientific Reports, 6:32279, 2016, 8 pages.
Liu et al., "Preparation of Modified Red Mud-Supported Fe Catalysts for Hydrogran Production by Catalytic Methane Decomposition," Article ID 8623463, Hindawi, Journal of Nanomaterials, 2017, 11 pages.
Researchandmarkets.com [online], "Global 1 Butene Demand—Supply and Price Analysis," 2002-2021, retrieved on Jan. 26, 2021, retrieved from URL <https://www.researchandmarkets.com/reports/3752113/global-1-butene-demand-supply-and-price-analysis>, 1 page.
PCT International Search Report and Written Opinion in International Appln. No. PCT/US2021/036161, dated Sep. 9, 2021, 13 pages.
Sushil et al., "Catalytic applications of red mud, an aluminium industry waste: A review," Applied Catalysis B. Environmental, May 2008, 81(1-2): 64-77, 14 pages.

RED MUD AS A CATALYST FOR THE ISOMERIZATION OF OLEFINS

BACKGROUND

The polymerization of olefins often uses comonomers to affect the final properties, such as density, crystallinity, and the like. The comonomers are generally alpha-olefins, such as 1-butene, 1-hexene, and 1-octene, among others. Alpha-olefins are also important feedstocks for numerous other products, including additives for drilling fluids, lubricants, synthetic oils, plasticizers, and other products.

One of the most important alpha-olefins is 1-butene. The market size projection for 1-butene has been projected to pass four billion USD in 20210. Satisfying the projected demand for 1-butene through the currently used method of ethylene dimerization may be impractical due to costs and its competitive use in polyethylene.

SUMMARY

An embodiment described herein provides a method for using red mud as a catalyst for isomerization of olefins. The method includes calcining the red mud, flowing an olefin feedstock over the red mud in an isomerization reactor, and separating an alpha-olefin from a reactor effluent.

An embodiment described herein provides an isomerization unit for producing an alpha-olefin product stream from an olefin feedstock. The isomerization unit includes an upstream purification system to separate a feed stream that comprises olefins from an initial feedstock, generating the olefin feedstock. The isomerization unit includes a reactor comprising a red mud catalyst to isomerize the olefins to form an alpha-olefin and a product purification system to isolate the alpha olefin product stream from an effluent from the reactor.

DETAILED DESCRIPTION

One method for the production of alpha-olefins is the isomerization of, which is an available material in refineries. The isomerization proceeds with aid of catalysts, such as $SiO_2$, $TiCl_3$, organo-aluminum, or zinc chromium ferrite ($ZnxCr_yFe_zO_4$), acidized clay, alumina, or MgO catalysts, among others. However, research into low cost, durable, selective and efficient catalysts is still needed.

Methods for the use of red mud as a catalyst for the isomerization is described herein. Red mud is a waste product generated during alumina production in the Bayer process, which is responsible for more than 95% of all alumina produced in the world. In this process, each ton of aluminum oxide that is produced results in 0.3 to 2.5 tons of bauxite tailings, or red mud. As a consequence, about 155 million tons of red mud are created annually with worldwide storage at over 3.5 billion tons in 2014. Accordingly, red mud is a low cost material that is in high supply. Although red mud has significant heterogeneity, the generic composition is shown in Table 1. The complex mixture of metals indicates that red mud may be an effective catalyst for the isomerization of olefins, such as 2-butene to 1-butene described in examples herein.

TABLE 1

| The generic composition of global red mud | | | | | |
|---|---|---|---|---|---|
| Component | $Fe_2O_3$ | $Al_2O_3$ | $SiO_2$ | $Na_2O$ | CaO | $TiO_2$ |
| Percentage | 30-60% | 10-20% | 3-50% | 2-10% | 2-8% | 10% |

Figure 1:
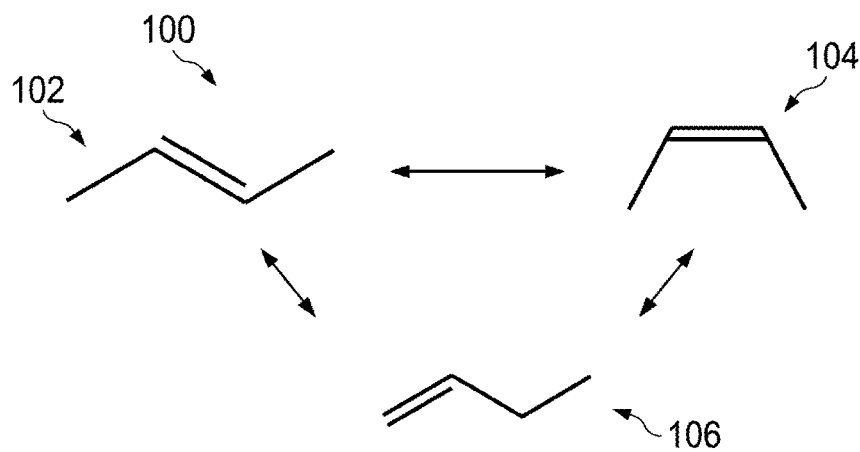
FIG. 1 is reaction scheme showing the inter-conversions of 2-butene and 1-butene by isomerization.

FIG. 1 is reaction scheme 100 showing the inter-conversions of 2-butene and 1-butene by isomerization. In the reaction scheme 100, trans-2-butene 102, cis-2-butene 104, and 1-butene 106 can be isomerized to each other. The lowest energy configuration is the trans-2-butene 102, and, thus, a catalyst is used to form the 1-butene 106. Similar interconversions may be used in the isomerization of other olefins.

As described herein, red mud is used as the catalyst to isomerize the 2-butene isomers 102 and 104 to produce 1-butene. This takes advantage of the mixture of metals constituting red mud, which include Ti, Fe and Al. The mixture of the metal compounds in the red mud may enhance the isomerization yield and selectivity, for example, as compared to MgO or $SiO_2$ catalysts. Further, red mud is a waste material of negligible cost, which improves the competitive advantage over synthesized catalysts containing MgO or $SiO_2$. Accordingly, even at comparable rates of isomerization yield and selectivity, the low cost of the red mud makes its use favorable over higher cost catalysts.

Figure 2:
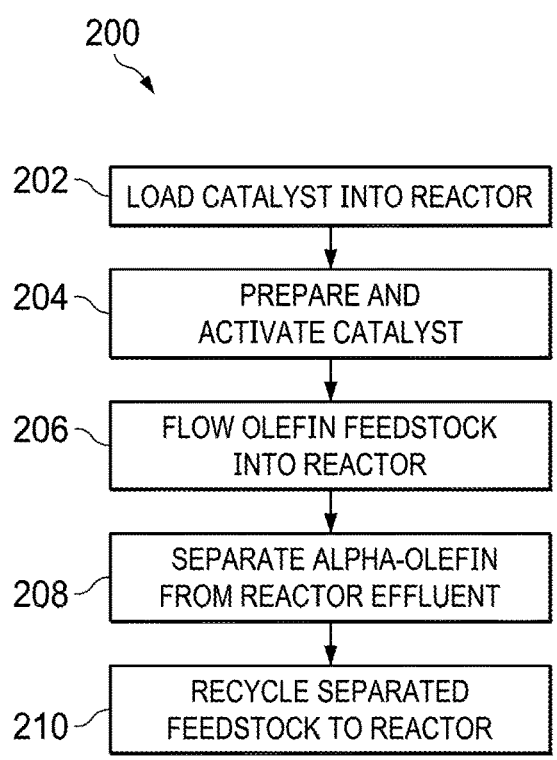
FIG. 2 is a method 200 for using a red mud catalyst to isomerize olefins in a feedstock to alpha-olefins.

FIG. 2 is a method 200 for using a red mud catalyst to isomerize olefins in a feedstock to alpha-olefins. In an embodiment, the method 200 is used to isomerize 2-butenes to 1-butene.

The method 200 begins at block 202, with loading the catalyst into the reactor. At block 204, the catalyst is prepared and activated. As red mud is a common waste material that is being used as supplied, the preparation is minimal. As described in the examples, the red mud is heated to drive off excess moisture and volatile components. The drying is performed under air at a temperature of between about 500° C. and about 800° C., or at a temperature of between 600° C. and about 700° C., or at about 650° C. The drying may be performed for between about 10 minutes (min.) and about 150 min., or for between about 30 min. and about 130 min., or for about 45 min. The catalyst is further calcined for activation, for example, by the generation of surface groups. The activation may be performed under a flow of an inert gas. The activation is performed at a temperature of between about 400° C. and about 700° C., or at a temperature of between 500° C. and about 600° C., or at about 650° C. The activation may be performed for between about 2 hours and about 6 hours, or for between about 3 hours and about 5 hours, or for about 4 hours.

In commercial usage, the catalyst may be dried and activated at a remote production facility, before being brought to the isomerization unit and loaded into the reactor. Any number of combinations of this may be performed. For example, the catalyst may be dried at the remote production facility and activated after being loaded into the commercial isomerization reactor.

At block 206, the olefin feedstock, such as a 2-butene feedstock, is flowed into the reactor for isomerization into the other alpha-olefins, such as 1-butene. In some embodiments described herein, the 2-butene feedstock is a mixture of cis-2-butene and trans-2-butene, for example, at a 50-50 ratio. In various embodiments, such as in commercial usage, the 2-butene feedstock is a refinery stream that includes a number of hydrocarbons with boiling points in a range, such as a light fraction from a hydrocracking unit, for example, having a boiling point range of about −30° C. to about 40° C., about −20° C. to about 10° C., or about −10° C. to about 0° C. A narrower range of boiling points may be indicative of a feedstock that is higher in cis-2-butene and trans-2-butene, providing a higher purity 1-butene product stream, and decreasing the purification needed downstream before sales. The butene feedstock is flowed through the reactor at a weight-hour space velocity (WHSV) ($hr^{-1}$) of between about 400 $hr^{-1}$ and about 1400 $hr^{-1}$, or between about 650 $hr^{-1}$ and about 1150 $hr^{-1}$, or about 900 $hr^{-1}$.

At block 208, the alpha-olefin, or 1-butene, product is separated from the reactor effluent. The alpha-olefin, or 1-butene, may then be provided to other processes, such as polymerization of polyolefins. At block 210, the separated effluent, for example, including unreacted olefins, such as 2-butene, may be recycled to the reactor to increase yields. The separated effluent may be sent to purification systems upstream of the reactor to remove other hydrocarbons or may be provided directly to the reactor, for example, by being mixed with the initial feedstock.

Figure 3:
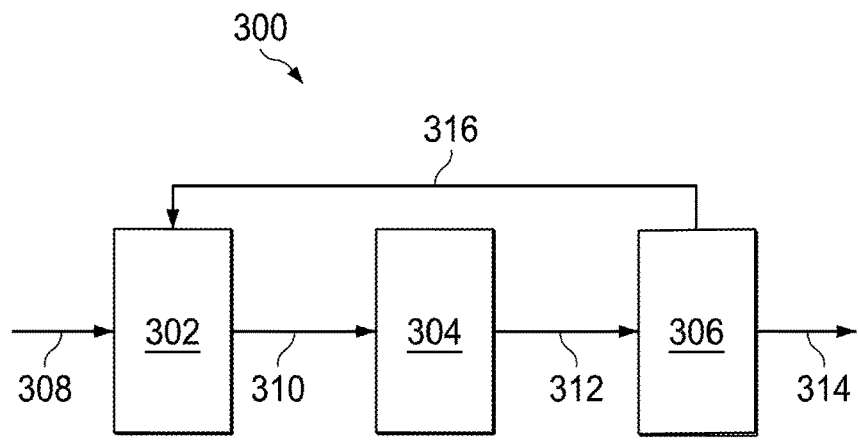
FIG. 3 is an isomerization unit 300 for producing an alpha-olefin from an olefin feedstock, using a red mud catalyst.

FIG. 3 is an isomerization unit 300 for producing an alpha-olefin from an olefin feedstock, using a red mud catalyst. In some embodiments, the isomerization unit 300 is used for producing 1-butene from 2-butene. The isomerization unit 300 may be part of a refinery system, producing a number of different hydrocarbon streams. In this example, the isomerization unit 300 includes three units, an upstream purification system 302, a reactor 304, and a product purification system 306.

The initial feedstock 308 is fed to the upstream purification system 302. In various embodiments, the upstream purification system 302 includes a distillation column, a cryogenic distillation column, a flash vessel, and the like. Other streams (not shown), having different boiling point ranges, are separated out in the upstream purification system 302 and sent to another processing units. An isomerization feedstock stream 310, for example, having a boiling point range that includes trans-2-butene and cis-2-butene, is provided to the reactor 304.

In the reactor 304, the isomerization feedstock stream 310 is flowed over the red mud, which catalyzes the isomerization reaction of at least a portion of the olefins to an alpha-olefin product, such as catalyzing a portion of 2-butene feedstocks to a 1-butene product. A reactor effluent stream 312 is then provided to the product purification system 306. In some embodiments, the reactor 304 is a standard isomerization reactor used in a refinery.

In the product purification system 306, the alpha-olefin product stream, such as the 1-butene product, is separated and provided as product stream 314. In various embodiments, the product purification system 306 includes a distillation column, a cryogenic distillation column, a flash vessel, and the like. The alpha-olefin product stream 314 may be sold to polyolefin manufacturers, used in other processes to form other products, and the like. Other streams (not shown) from the product purification system 306 may be sent to other processing units. In some implementations, a recycle stream 316 is returned from the product purification system 306 to the upstream purification system 302 after removal of the alpha-olefin product. In some embodiments, this may be performed to allow the recovery of unreacted trans-2-butene and cis-2-butene to increase the overall yield of the process. In other embodiments, the recycle stream 316 is combined with the isomerization feedstock stream 310 directly, and fed to the reactor 304.

Examples

To demonstrate the use of red mud as an isomerization catalyst, feed streams including 2-butenes were isomerized to 1-butene. The products were analyzed to determine the yields and selectivities of the red mud catalyst.

Elemental analyses were performed by X-ray Fluorescence (XRF) analysis. The XRF analysis was performed on a Horiba® XGT-7200. The X-ray tube is equipped with an Rh target, voltage was set at 30 kV, no X-ray filter was used, and analysis preset time was 400 s. Before measurement, samples were placed on a double-sized tape (NICETACK™, Prod. No NW-15) and then placed in the chamber, which was then degassed. The results are an average of four measurements were taken. The general composition of Saudi Arabian red mud is shown in Table 2. The red mud composition listed in Table 2 is the comprehensive composition, which includes both major and minor constituents.

TABLE 2

Typical composition of Saudi Arabian Red Mud in weight percent.

| Component | RM |
| --- | --- |
| $Al_2O_3$ | 23.34 |
| CaO | 6.82 |
| $CeO_2$ | 0.09 |
| Cl | 0.03 |
| $Cr_2O_3$ | 0.15 |
| $Fe_2O_3$ | 29.45 |
| $Ga_2O_3$ | 0.01 |
| $HfO_2$ | 0.1 |
| $K_2O$ | 0.07 |
| MgO | 0.07 |
| MnO | 0.06 |
| $Na_2O$ | 4.74 |
| $Nb_2O_5$ | 0.03 |
| $P_2O_5$ | 0.16 |
| PbO | 0.03 |
| $Sc_2O_3$ | 0.02 |
| $SiO_2$ | 23.1 |
| $SO_3$ | 0.09 |
| SrO | 0.36 |
| $ThO_2$ | 0.02 |
| $TiO_2$ | 10 |
| ZnO | 0.01 |
| $ZrO_2$ | 0.43 |
| $Y_2O_3$ | 0.02 |

TABLE 3

Composition of Experimental Saudi Arabian red mud in weight percent.

| Component | $Fe_2O_3$ | $Al_2O_3$ | $SiO_2$ | $Na_2O$ | CaO | $Ti_2O$ |
| --- | --- | --- | --- | --- | --- | --- |
| Percentage | 18.75 | 25.22 | 18.88 | 11.7 | 7.97 | 6.89 |

The performance of a Saudi Arabian red mud sample in the isomerization of a mixture of trans-2-butene and cis-2-butene to 1-butene was evaluated at different temperatures, 450° C., 500° C. and 550° C. An example of an elemental composition of a Saudi Arabian red mud sample used for runs herein is shown in Table 3. The composition listed in Table 3 is only for the major constituents that are always reported in literature as red mud composition. As red mud is a waste material the composition is heterogeneous, with a 5%, or higher, variation in the composition. This can be seen in the comparison of the $Fe_2O_3$ amounts in Table 2 versus Table 3. The variation in composition does not substantially affect the products or selectivity.

The results of the isomerization were compared to MgO and $SiO_2$ commercial catalysts. The experimental runs were performed in a BTRS reactor unit from Autoclave Engineers division of Parker Hannifin Corp, having 9 mm ID and 30 cm length. The reactor is SS steel reactor with 4 different MFC units to control the flowing gases. Maximum capacity of the reactor system is 800 C and can withstand up to 20 bar of reaction pressure. The amount of catalyst used in each run was 2 mL (0.65 g).

Figure 4:
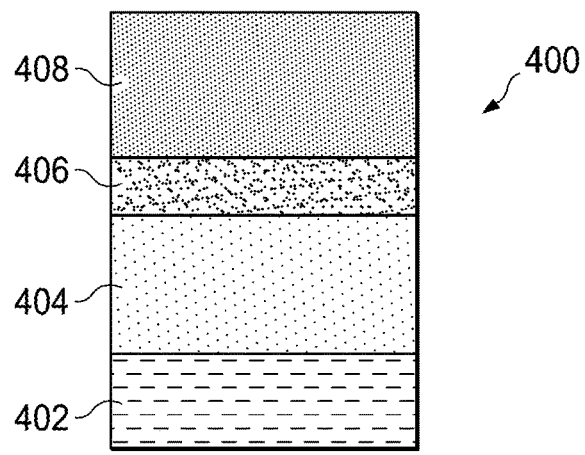
FIG. 4 is a schematic diagram of an experimental tube reactor 400 for testing the conversion of 2-butene to 1-butene using a red mud catalyst.

FIG. 4 is a schematic diagram of an experimental tube reactor 400 for testing the conversion of 2-butene to 1-butene using a red mud catalyst. To hold the material in place a layer of quartz wool 402 is inserted into the experimental reactor tube 400. An initial layer 404 of 14 g of silicon carbide are poured over the quartz wool 402. A catalyst layer 406 including about 2 mL of catalyst is inserted into the experimental tube reactor 400. For the red mud catalyst, the 2 mL corresponds to about 0.65 g. Finally, a top layer 408 of about 17 g of silicon carbide is poured over the catalyst layer 406. The experimental reactor tube 400 is then inserted into the BTRS catalyst testing system. Prior to evaluation each catalyst sample was calcined under air at 650° C. to remove moisture or volatile gases, if present. The catalyst sample was then activated at 550° C. inside the reactor for 4 hrs under nitrogen. The 2-butene feed is a mixture of 50% cis-2-butene and 50% trans-2-butene. The concentration of 2-butene employed in the evaluation was 15% (5 ml) diluted with $N_2$ (25 ml).

The amounts of hydrocarbons in the reactor effluent streams were measured by gas chromatography. This was performed using an Agilent GC-7890B instrument from Agilent. The column was a capillary (HP-Al/KCL (50 m×0.53 mm×15 microns) column with an $N_2$ stationary phase and He carrier gas. A hybrid detector including a flame ionization detector (FID) and a thermal conductivity detector (TCD) was used. The flow rate of the carrier gas was 15 ml/min. After injection, a temperature ramp from 50° C. to 170° C. over 10 min. was performed, then the temperature was held at 220° C. for 15 min., before being cooled to the starting temperature.

From the GC results, yields and selectivities were calculated by the following formulas:

$$Yield = Conversion\ of\ butenes \times Selectivity\ of\ the\ product\ (1\text{-}butene)$$

$$Conversion = 100 - (CisButene\ Yield + TransButene\ Yield)$$

$$Conversion\text{-}C4 = 100 - (Cis\text{-}2\text{-}Butene\ Yield + Trans\text{-}2\text{-}Butene\ Yield)$$

$$Selectivity = \frac{Yield\ of\ Product}{Conversion} \times 100$$

In these formulas, yield represents the yield of 1-butene through the GC Retention Factor, and the conversion of 2-butene (cis & trans 2-butene) is obtained though GC retention factor.

Figure 5:
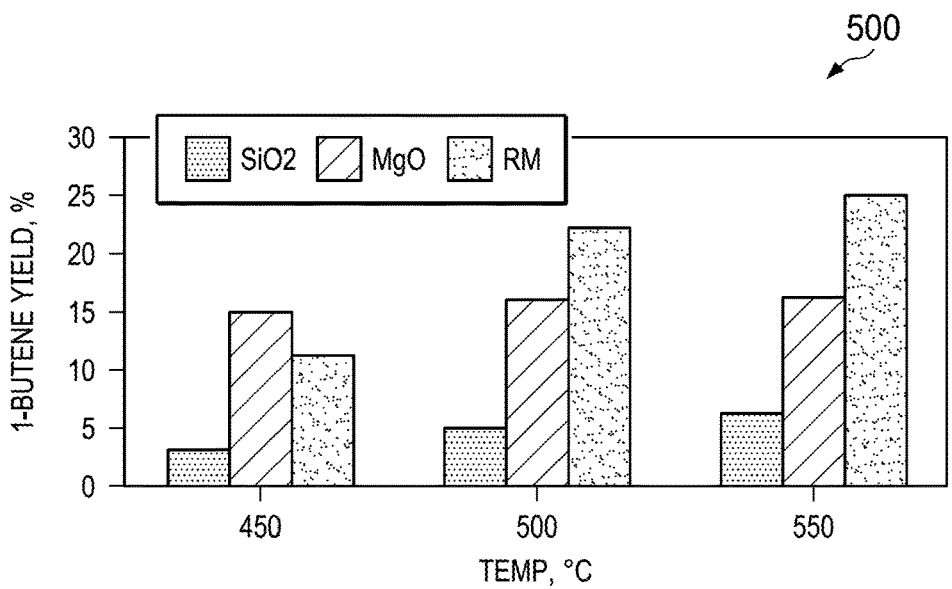
FIG. 5 is a bar chart showing the comparative yield of three catalysts in the conversion of 2-butene to 1-butene.

FIG. 5 is a bar chart 500 showing the comparative yield of three catalysts in the conversion of 2-butene to 1-butene. At all three tested temperatures, red mud provided significantly higher yield of 1-butene than $SiO_2$. Further, red mud provided higher yield to 1-butene than MgO at 500° C. and 550° C. However, at 450° C. MgO was relatively better than red mud and substantially outperformed $SiO_2$.

Figure 6:
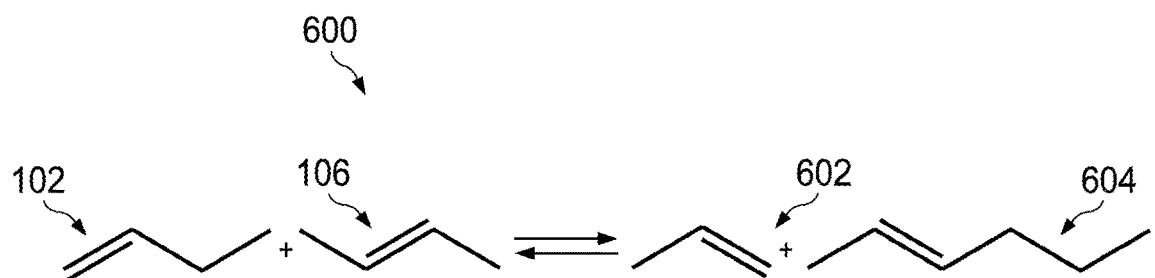
FIG. 6 is a reaction scheme 600 showing the formation of hydrocarbon contaminants from the reaction of 1-butene and 2-butene.

FIG. 6 is a reaction scheme 600 showing the formation of hydrocarbon contaminants from the reaction of 1-butene and 2-butene. Like numbered items are as described with respect to FIG. 1. In the reaction scheme 600, a metathesis reaction of 1-butene with trans-2-butene forms propylene 602 and 2-methylpentene 604. This reaction proceeds in the presence of 1-butene 102 and 2-butene 106 (cis and trans). If 2-butene is not present, it may be formed by an isomerization reaction allowing the metathesis reaction to occur. Accordingly, understanding the selectivity of the catalyst towards the formation of 1-butene is important.

Figure 7A:
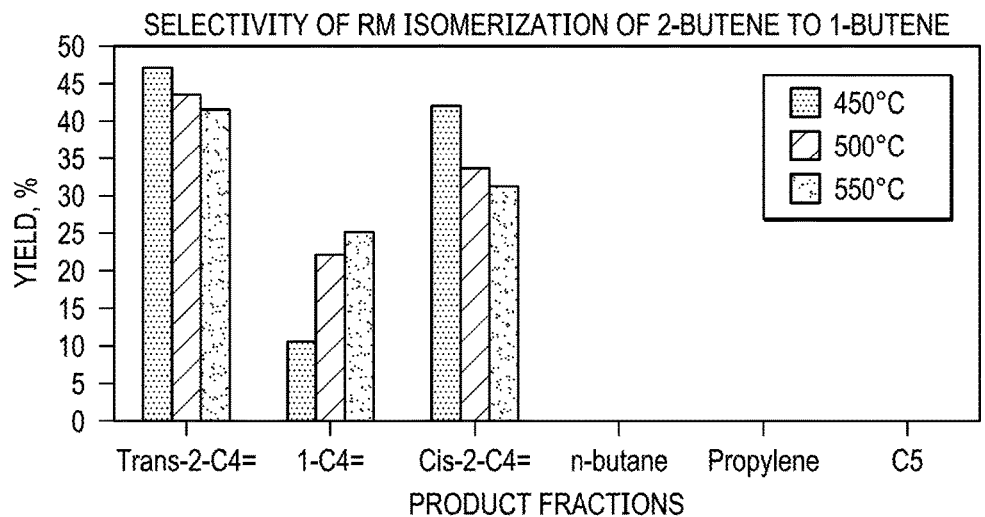
FIGS. 7A-7C are bar charts showing the comparative selectivity of three catalysts in the conversion of 2-butene to 1-butene.
Figure 7B:
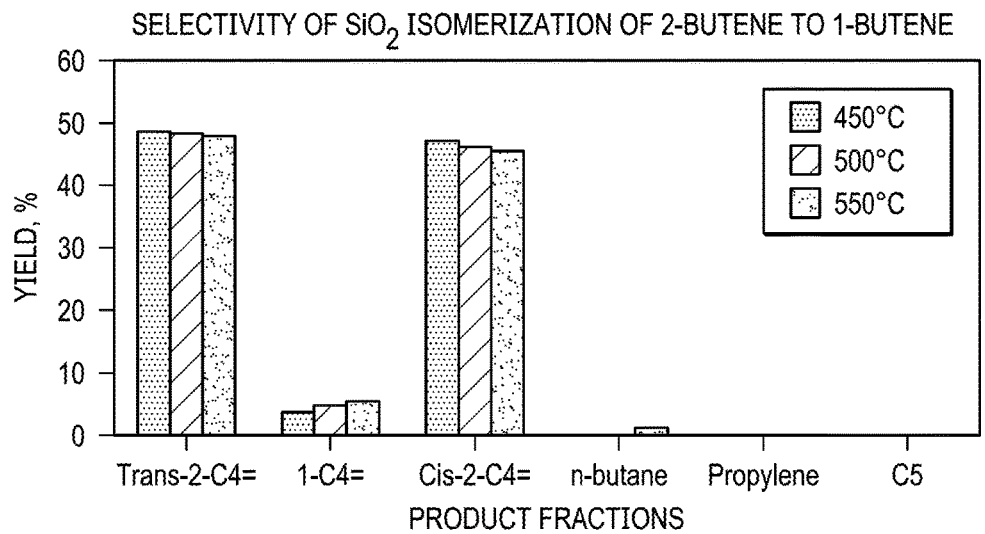
Figure 7C:
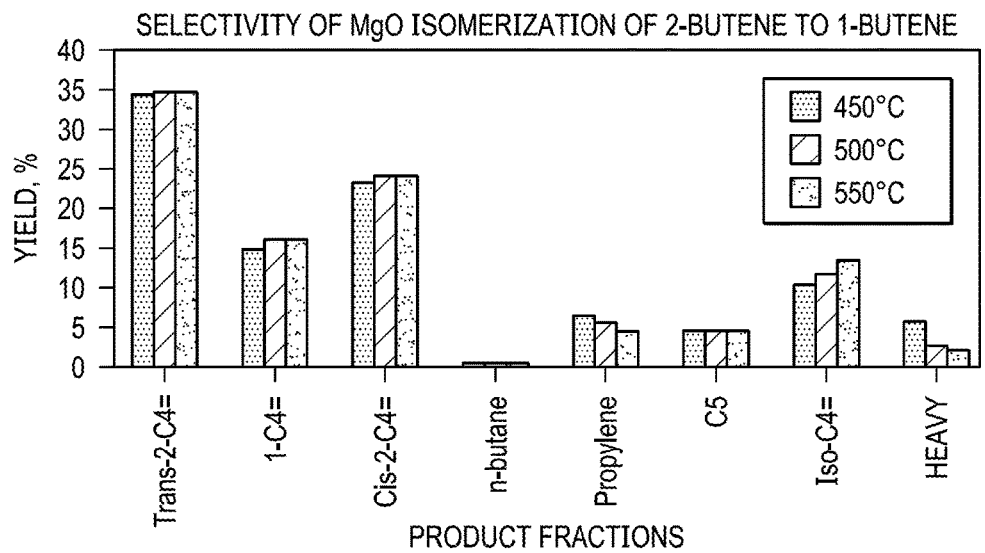

FIGS. 7A-7C are bar charts showing the comparative selectivity of three catalysts in the conversion of 2-butene to 1-butene. In FIG. 7A, the selectivity of the red mud isomerization of 2-butene to 1-butene is shown. This reaction follows the reaction scheme shown in FIG. 1, without the formation of other products. In contrast, the isomerization of 2-butene to 1-butene using an $SiO_2$ catalysts, shown in FIG. 7B, indicates that some amount of n-butane and a small amount of propylene were formed, in addition to far less 1-butene. Although MgO catalysts have higher formation of 1-butene in the isomerization then for the $SiO_2$ catalysts, as shown in FIG. 7C, a number of hydrocarbon byproducts were also formed. These include n-butane, propylene, $C_5$s, isobutene, and some heavy fractions An embodiment described herein provides a method for using red mud as a catalyst for isomerization of olefins. The method includes calcining the red mud, flowing an olefin feedstock over the red mud in an isomerization reactor, and separating alpha-olefins from a reactor effluent. In an aspect, the isomerization includes forming 1-butene from a feedstock comprising 2-butene.

In an aspect, the method includes calcining the catalyst to dry the catalyst, remove volatile gas, or both, at a temperature of between about 500° C. and about 800° C. for between about 10 minutes and about 150 minutes. In an aspect, the method includes calcining the catalyst to dry the catalyst, remove volatile gas, or both, at a temperature of between about 600° C. and about 700° C. for between about 30 minutes and about 130 minutes. In an aspect, the method includes calcining the catalyst to dry the catalyst, remove volatile gas, or both, at a temperature of about 650° C. for about 45 minutes.

In an aspect, the method includes calcining the catalyst to activate the catalyst at a temperature of between about 400° C. and about 700° C. for between about 2 hours and about 6 hours. In an aspect, the method includes calcining the catalyst to activate the catalyst at a temperature of between about 400° C. and about 700° C. for between about 2 hours and about 6 hours. In an aspect, the method includes calcining the catalyst to activate the catalyst at a temperature of about 650° C. for about 4 hours.

In an aspect, the method includes obtaining the butene feedstock from an upstream purification system in a refinery. In an aspect, the method includes obtaining the butene feedstock with a boiling point range of between about −30° C. and about 40° C. In an aspect, the method includes obtaining the butene feedstock with a boiling point range of between about −20° C. and about 10° C. In an aspect, the method includes obtaining the butene feedstock with a boiling point range of between about −10° C. and about 0° C.

In an aspect, the method includes flowing the butene feedstock over the red mud at a weight hour space velocity of between about 400 $hr^{-1}$ and 1300 $hr^{-1}$. In an aspect, the method includes flowing the butene feedstock over the red mud at a weight hour space velocity of between about 650 $hr^{-1}$ and about 1150 $hr^{-1}$. In an aspect, the method includes flowing the butene feedstock over the red mud at a weight hour space velocity of about 900 $hr^{-1}$.

In an aspect, the method includes separating the 1-butene from the reactor effluent in a distillation column. In an aspect, the method includes returning the reactor effluent to an upstream purification system after removal of the 1-butene from the reactor effluent. In an aspect, the method includes combining the reactor effluent with the butene feedstock after separating the 1-butene from the reactor effluent.

An embodiment described herein provides an isomerization unit for producing an alpha-olefin product stream from an olefin feedstock. The isomerization unit includes an upstream purification system to separate a feed stream that includes olefins from an initial feedstock, generating the olefin feedstock. The isomerization unit includes a reactor comprising a red mud catalyst to isomerize the olefins to form an alpha-olefin, and a product purification system to isolate the alpha-olefin product stream from an effluent from the reactor. In an aspect, the feed stream comprises trans-2-butene and cis-2-butene and the alpha-olefin product stream comprises 1-butene In an aspect, the butene feedstock has a boiling point range of about –20° C. to about 10° C. In an aspect, the product purification system includes a distillation column configured to recycle the effluent to the upstream purification system, after removal of the 1-butene product stream.

Other implementations are also within the scope of the following claims.

What is claimed is:

1. A method for isomerization of olefins comprising:
calcining a red mud catalyst;
isomerizing an olefin feedstock over the calcined red mud catalyst in a reactor to form an effluent; and
separating the effluent to obtain an alpha-olefin stream and an alpha-olefin depleted stream.

2. The method of claim 1, wherein the olefin feedstock comprises 2-butene and the effluent comprises 1-butene.

3. The method of claim 1, wherein the calcining is conducted to dry the catalyst, remove volatile gases, or both, at a temperature of between about 500° C. and about 800° C. for between about 10 minutes and about 150 minutes.

4. The method of claim 1, wherein the calcining is conducted to dry the catalyst, remove volatile gases, or both, at a temperature of between about 600° C. and about 700° C. for between about 30 minutes and about 130 minutes.

5. The method of claim 1, wherein the calcining is conducted to dry the catalyst, remove volatile gases, or both, at a temperature of about 650° C. for about 45 minutes.

6. The method of claim 1, further comprising activating the calcined catalyst at a temperature of between about 400° C. and about 700° C. for between about 2 hours and about 6 hours.

7. The method of claim 1, further comprising activating the calcined catalyst at a temperature of between about 500° C. and about 600° C. for between about 3 hours and about 5 hours.

8. The method of claim 1, further comprising activating the calcined catalyst at a temperature of about 650° C. for about 4 hours.

9. The method of claim 1, wherein the olefin feedstock is obtained from an upstream purification system in a refinery.

10. The method of claim 1, wherein the olefin feedstock has a boiling point range of between about –30° C. and about 40° C. and comprises butene.

11. The method of claim 1, wherein the olefin feedstock has a boiling point range of between about –20° C. and about 10° C. and comprises butene.

12. The method of claim 1, wherein the olefin feedstock has a boiling point range of between about –10° C. and about 0° C. and comprises butene.

13. The method of claim 1, further comprising flowing the feedstock over the red mud at a weight hour space velocity of between about 400 $hr^{-1}$ and 1300 $hr^{-1}$.

14. The method of claim 1, further comprising flowing the feedstock over the red mud at a weight hour space velocity of between about 650 $hr^{-1}$ and 1150 $hr^{-1}$.

15. The method of claim 1, further comprising flowing the feedstock over the red mud at a weight hour space velocity of about 900 $hr^{-1}$.

16. The method of claim 1, wherein the separating is performed in a distillation column.

17. The method of claim 1, wherein the alpha-olefin stream comprises 1-butene and the separating is performed in a distillation column.

18. The method of claim 1, further comprising passing the alpha-olefin depleted stream to an upstream purification system.

19. The method of claim 1, further comprising combining the alpha-olefin depleted stream with the olefin feedstock.

* * * * *